US012751987B2

(12) United States Patent
Lin et al.

(10) Patent No.: US 12,751,987 B2
(45) Date of Patent: Oct. 6, 2026

(54) METHODS FOR REDUCING SKIN PORPHYRIN CONTENT AND INCIDDENCE OF ACNES, OR INCREASING FERRITIN CONTENT WITHIN INTESTINAL CELLS BY USING QUEEN PLUM EXTRACT

(71) Applicant: TCI CO., LTD., Taipei (TW)

(72) Inventors: Yung-Hsiang Lin, Taipei (TW); Fan-Jhen Dai, Taipei (TW); Yin-Di Su, Taipei (TW)

(73) Assignee: TCI CO., LTD., Taipei (TW)

( * ) Notice: Subject to any disclaimer, the term of this patent is extended or adjusted under 35 U.S.C. 154(b) by 317 days.

(21) Appl. No.: 18/528,808

(22) Filed: Dec. 5, 2023

(65) Prior Publication Data

US 2024/0207347 A1 Jun. 27, 2024

Related U.S. Application Data

(60) Provisional application No. 63/386,173, filed on Dec. 6, 2022.

(51) Int. Cl.

| | |
|---|---|
| ***A61K 36/736*** | (2006.01) |
| ***A61K 8/9789*** | (2017.01) |
| ***A61K 31/702*** | (2006.01) |
| ***A61P 7/06*** | (2006.01) |
| ***A61P 17/10*** | (2006.01) |
| ***A61Q 17/04*** | (2006.01) |

(52) U.S. Cl.

CPC .......... *A61K 36/736* (2013.01); *A61K 8/9789* (2017.08); *A61K 31/702* (2013.01); *A61P 7/06* (2018.01); *A61P 17/10* (2018.01); *A61Q 17/04* (2013.01)

(58) Field of Classification Search

CPC .. A61K 36/736; A61K 8/9789; A61K 31/702; A61K 2236/33; A61K 2236/39; A61K 2800/522; A61P 7/06; A61P 17/10; A61Q 17/04; A61Q 19/00; A61Q 19/08

See application file for complete search history.

(56) References Cited

U.S. PATENT DOCUMENTS

2012/0276025 A1* 11/2012 Florence ................ A61K 8/062 424/769

OTHER PUBLICATIONS

Guo, Ting "Processing Method Of Prunus Salicina Juice". CN 110897063 A, filed Dec. 4, 2019, and published Mar. 24, 2020—English translation (Year: 2020).*

Kim, Eunki. "Pharmaceutical Composition For Preventing Or Treating Vitiligo Comprising Extract Of Prunus Salicina Extract As An Active Ingredient". KR 20210006085 A, filed Jul. 8, 2019, and published Jan. 18, 2021—English translation (Year: 2021).*

Kim Young, Chul. "Composition For Improving Skin Condition Comprising Extract From Plum As Active Ingredient". KR 20140125234 A, filed Apr. 18, 2013, and published Oct. 28, 2014—English translation (Year: 2014).*

Igwe EO, Charlton KE. A Systematic Review on the Health Effects of Plums (*Prunus domestica* and *Prunus salicina*). Phytother Res. vol. 30, issue. 5, pp. 701-731. doi: 10.1002/ptr.5581 (Year: 2016).*

Schieber M, Chandel NS. ROS function in redox signaling and oxidative stress. Curr Biol. vol. 24, issue. 10, pp. R453-R462 doi: 10.1016/j.cub.2014.03.034. (Year: 2014).*

Wortzman M, Nelson DB. A comprehensive topical antioxidant inhibits oxidative stress induced by blue light exposure and cigarette smoke in human skin tissue. J Cosmet Dermatol. vol. 20, issue. 4, pp. 1160-1165 doi: 10.1111/jocd.13991. (Year: 2021).*

Examination report dated May 10, 2024, listed in correspondent Taiwan patent application No. 112147322 (publication No. 202423468).

NE-Queen-Garnet-Extract-Datasheet, v1.0, Native Extracts Pty Ltd., May 10, 2021, https://www.canadiancosmeticcluster.com/uploads/3/7/9/8/37984461/ne-queen-garnet-extract-datasheet-v1. 0-2021-05-10.pdf Full text, especially title, ingredient descriptions, the right column.

* cited by examiner

*Primary Examiner* — Susan Hoffman
*Assistant Examiner* — Nashara L Moreau
(74) *Attorney, Agent, or Firm* — Chich-Mei Wang

(57) ABSTRACT

A method for inhibiting skin damage caused by blue light, reducing skin sagging, reducing skin porphyrin content, or increasing ferritin content in a subject in need thereof is provided. The method includes: administering to the subject an effective dose of queen plum extract. The queen plum extract is obtained by extracting whole fruit of *Prunus salicina* by water. The queen plum extract has at least one of the following effects: inhibiting skin damage caused by blue light, improving skin sagging, reducing skin porphyrin content or increasing ferritin content.

4 Claims, 10 Drawing Sheets

Specification includes a Sequence Listing.

METHODS FOR REDUCING SKIN PORPHYRIN CONTENT AND INCIDDENCE OF ACNES, OR INCREASING FERRITIN CONTENT WITHIN INTESTINAL CELLS BY USING QUEEN PLUM EXTRACT

CROSS-REFERENCE TO RELATED APPLICATION

This application claims the benefit of U.S. provisional application Ser. No. 63/386,173, filed on Dec. 6, 2022. The entirety of the above-mentioned patent application is hereby incorporated by reference herein and made a part of the specification.

REFERENCE OF AN ELECTRONIC SEQUENCE LISTING

The contents of the electronic sequence listing (P223936USI.xml; Size: 10,079 bytes; and Date of Creation: Dec. 1, 2023) is herein incorporated by reference in its entirety.

BACKGROUND

Technical Field

The present invention relates to applications of *Prunus salicina*, and particularly relates to a method for using a queen plum extract, where the queen plum extract has the effects of inhibiting skin damage caused by blue light, improving skin sagging, reducing skin porphyrin content, increasing ferritin content or the like.

Related Art

A common variety of plums ripen from the inside out. Therefore, they need to be picked off before ripening, and then are placed in a suitable environment to wait for them to ripen. *Prunus salicina*, a specialty of Queensland, Australia, ripens from the outside in, also known as queen plum. Therefore, the *Prunus salicina* in trees is picked until the flesh becomes soft and dark purple. The *Prunus salicina* receives sunlight for a longer period of time and can effectively resist the damage of sunlight.

The *Prunus salicina* is produced in Queensland, Australia. Queensland is commonly known as a bright sun state, its state border is close to 23.5° in the southern hemisphere, and its environment is irradiated with the sun for a long time. Therefore, the *Prunus salicina* from Queensland, Australia, receives more sunlight for a longer period of time, and longer sunlight can effectively promote production of nutrients in the *Prunus salicina*.

SUMMARY

In view of this, in order to further seek a wider range of new applications of *Prunus salicina*, the present invention provides use of a queen plum extract, where the queen plum extract is used for preparing a composition for inhibiting skin damage caused by blue light, improving skin sagging, reducing skin porphyrin content or increasing ferritin content.

In some embodiments, a method for inhibiting skin damage caused by blue light in a subject in need thereof is provided. The method include: administering to the subject an effective amount of queen plum extract, and the queen plum extract is obtained by extracting whole fruit of *Prunus salicina* by water.

In some embodiments, the queen plum extract promotes antioxidant capacity of skin of the subject.

In some embodiments, the queen plum extract reduces the amount of ROS produced by the skin of the subject in response to blue light irradiation.

In some embodiments, a method for reducing skin sagging are provided. The method include: administering to the subject an effective amount of queen plum extract, wherein the queen plum extract is obtained by extracting whole fruit of *Prunus salicina* by water.

In some embodiments, the queen plum extract promotes moisture retention capacity of skin of the subject.

In some embodiments, the queen plum extract improves skin elasticity of the subject.

In some embodiments, the queen plum extract improves collagen content of the subject.

In some embodiments, the queen plum extract enhances expression of a COL1A1 gene and/or a TIMP1 gene of the subject.

In some embodiments, the queen plum extract inhibits expression of an MMP9 gene of the subject.

In some embodiments, the queen plum extract promotes hyaluronan synthesis of the subject.

In some embodiments, the queen plum extract promotes expression of an HAS2 gene of the subject.

In some embodiments, the queen plum extract maintains an extracellular matrix of the subject.

In some embodiments, the queen plum extract enhances expression of an LOX gene of the subject.

In some embodiments, a method for reducing skin porphyrin content are provided. The method include: administering to the subject an effective amount of queen plum extract. The queen plum extract is obtained by extracting whole fruit of *Prunus salicina* by water. *Bacillus acnes* will secrete porphyrin, and a decrease in the amount of the porphyrin on the surface of skin indicates a lower number of *Bacillus acnes* and a lower incidence of acnes.

In some embodiments, the queen plum extract reduces incidence of acnes of the subject.

In some embodiments, a method for increasing ferritin content is provided. The method includes: administering to the subject an effective amount of queen plum extract, and the queen plum extract is obtained by extracting whole fruit of *Prunus salicina* by water.

In some embodiments, the queen plum extract includes cumoricanhydride. In some embodiments, the cumoricanhydride increases cell iron content of the subject.

In summary, the queen plum extract of any embodiment of the present disclosure can be used for preparing the composition for inhibiting skin damage caused by blue light, reducing skin sagging, reducing skin porphyrin content, or increasing ferritin content. In some embodiments, the queen plum extract has at least one of the following effects: promoting antioxidant capacity of the skin, reducing the amount of ROS produced by the skin in response to blue light irradiation, promoting moisture retention capacity of the skin, improving skin elasticity, improving collagen content, enhancing expression of COL1A1 gene and/or TIMP1 gene, inhibiting expression of MMP9 gene, promoting hyaluronan synthesis, promoting expression of HAS2 gene, maintaining the extracellular matrix, enhancing expression of LOX gene, and reducing incidence of acnes of the subject.

DETAILED DESCRIPTION

Figure 1:
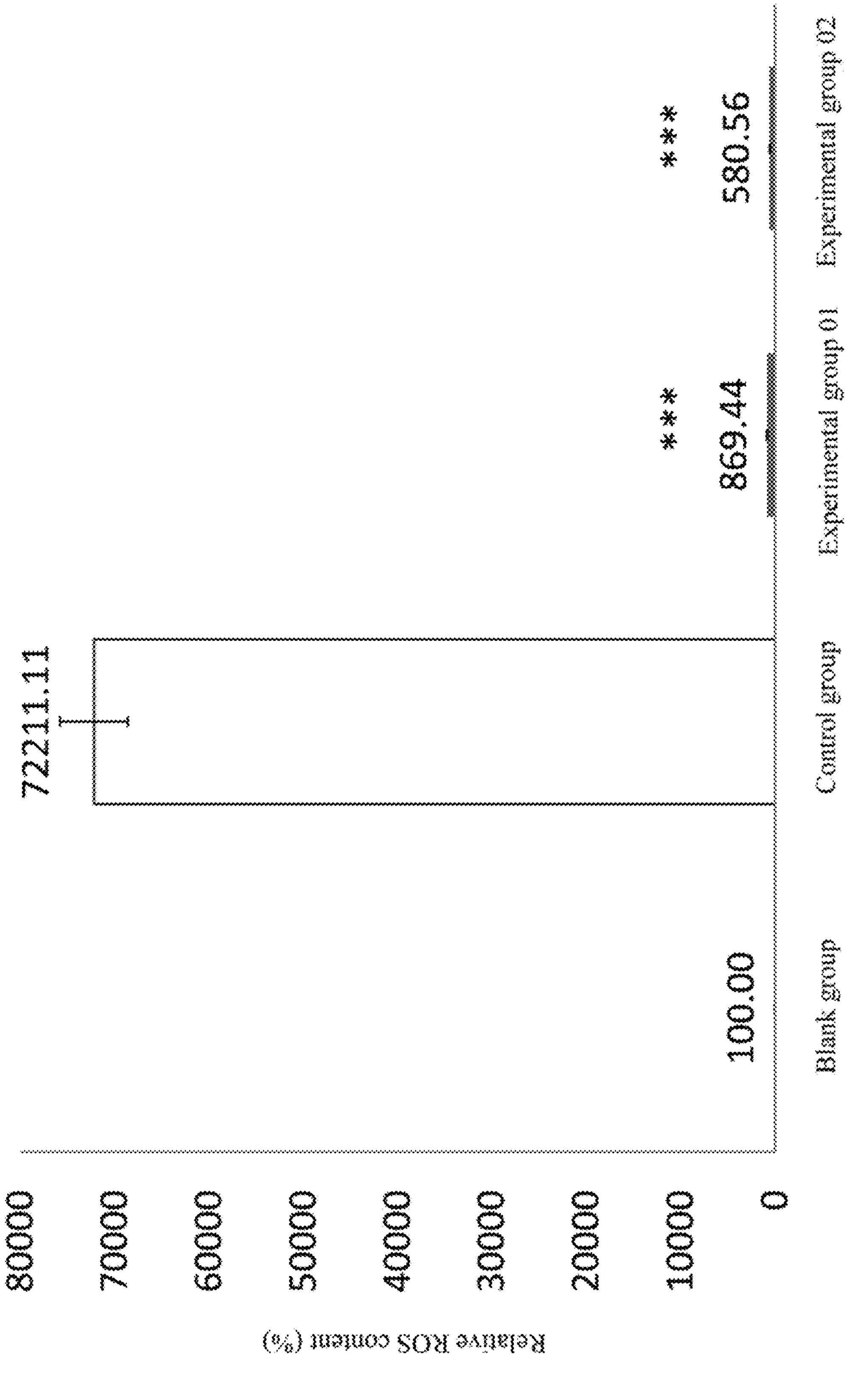
FIG. 1 is a bar chart showing the relative ROS content.

The term "extract" used herein refers to a product prepared by extraction. Here, the extract can be presented in the form of a solution of the extract dissolved in a solvent, or can be presented as a concentrate or essence without or substantially without the solvent.

As used herein, "*Prunus salicina*" refers to a deep purple complete fruit of a plum (scientific name: *Prunus salicina*) plant, also known as Queen Garnet plum. Here, the complete fruit includes peel, flesh, and a stone.

In some embodiments, a queen plum extract is prepared by a water extraction procedure. The water extraction procedure includes an extraction step. The extraction step is to extract whole fruit of *Prunus salicina* with water. In other words, an extraction solution is obtained by extracting active ingredients in the whole fruit of the *Prunus salicina* using water as a solvent. In some embodiments, the extraction step can be achieved by soaking the whole fruit of the *Prunus salicina* in water at a specific temperature for a specific time.

In some embodiments, the specific temperature refers to a temperature between 90° C. and 80° C. In some embodiments, the specific temperature is 85° C.±5° C. In some embodiments, the specific temperature is 85° C.

In some embodiments, the specific time refers to 50 min to 80 min.

In some embodiments, in the extraction step, the whole fruit may be a fresh queen plum fruit, a dried queen plum fruit, or a frozen queen plum fruit. In some embodiments, drying may be air drying, sun drying, drying in shade, or freeze drying. In some embodiments, in the extraction step, the whole fruit may refer to a complete fruit, or refer to a fruit that is further processed via chopping, dicing, milling, grinding, or otherwise to influence the size and physical integrity of a raw material. In some embodiments, in the extraction step, the *Prunus salicina* is *Prunus salicina* produced in Queensland, Australia.

In some embodiments, in the extraction step, the weight ratio of the *Prunus salicina* to water is 1:5.

In some embodiments, the water extraction procedure further includes an acceptance step. In some embodiments, the acceptance step refers to measuring Degrees Brix (° Bx) of an extraction solution after the extraction step is carried out for 60 min (i.e., a specific time is 60 min) and confirming that the Degrees Brix is 7.5±0.5° Bx. In some embodiments, if the measured Degrees Brix does not reach 7.5° Bx in the acceptance step, the extraction step is extended for an additional 30 min (i.e., a complete specific time is 90 min). That is, the stop time of the extraction step of the queen plum extract is determined by an acceptance criterion where the Degrees Brix is 7.5±0.5° Bx.

In some embodiments, the queen plum extract is subjected to the water extraction procedure further including a filtration step. After the extraction step is stopped, the filtration step can be carried out. The filtration step is to filter the extraction solution obtained from the extraction step via a sieve or centrifugation, in order to remove solid matter from the extraction solution. By way of examples, the filtration step may be to filter the extraction solution through a 400-mesh sieve to obtain a filtrate.

It should be understood that the extraction solution, the filtrate, or any combination thereof obtained from the aforementioned water extraction procedure may be used as the queen plum extract according to actual needs.

In some embodiments, a color number of the queen plum extract is between PANTONE 7420 U and PANTONE 7421 U.

In some embodiments, the queen plum extract may have at least one of the following effects: inhibiting skin damage caused by blue light, promoting antioxidant capacity of skin, reducing the number of ROS produced by blue light irradiation on the skin, reducing skin sagging, promoting moisture retention capacity of the skin, improving skin elasticity, improving collagen content, enhancing expression of a collagen synthesis gene (such as a COL1A1 gene and/or a TIMP1 gene), inhibiting degradation of collagen related genes (such as an MMP9 gene), enhancing expression of hyaluronan synthesis related genes (such as an HAS2 gene), maintaining an extracellular matrix, enhancing expression of an LOX gene, reducing skin porphyrin content, reducing incidence of acnes and increasing ferritin content. In other words, when administered to an individual, the queen plum extract can exhibit at least one of the aforementioned effects in the individual. Therefore, the queen plum extract is suitable for preparing a composition having at least one of the aforementioned effects. In some embodiments, the aforementioned individual may be a human. In some embodiments, in the aforementioned composition, the effective content of the queen plum extract is 0.5 g/d.

In some embodiments, the prepared composition may be a pharmaceutical product or an edible composition for non-medical purposes.

In some embodiments, the above-mentioned composition may be a pharmaceutical product. In other words, the pharmaceutical product includes an effective content of queen plum extract.

In some embodiments, the aforementioned pharmaceutical product can be made into a dosage form suitable for being intestinally or orally administrated, by using a technology well known to those skilled in the art. The dosage form suitable for being intestinally or orally administrated may be, but is not limited to, tablet, troche, lozenge, pill, capsule, dispersible powder or granule, solution, suspension, emulsion, syrup, elixir, slurry or analogues.

In some embodiments, the aforementioned pharmaceutical product can be made into a dosage form suitable for being parenterally or topically administrated, by using a technology well known to those skilled in the art. The dosage form suitable for being parenterally or topically administrated may be, but is not limited to, injection, sterile powder, external preparation and analogues. In some embodiments, the pharmaceutical product can be administered via parenteral routes selected from the group consisting of subcutaneous injection, intradermal injection, intradermal injection or intralesional injection.

In some embodiments, the pharmaceutical product may further include a pharmaceutically acceptable carrier that is widely used in a drug manufacturing technology. For example, the pharmaceutically acceptable carrier may include one or more of the following reagents: solvent, buffer, emulsifier, suspending agent, decomposer, disintegrating agent, dispersing agent, binding agent, excipient, stabilizing agent, chelating agent, diluent, gelling agent, preservative, wetting agent, lubricant, absorption delaying agent, liposome and analogues. Selection and number regarding these reagents falls within the scope of the professional quality and routine technology well known to those skilled in the art.

In some embodiments, the pharmaceutically acceptable carrier may further include a solvent selected from the group consisting of water, normal saline, phosphate buffered saline (PBS) and an aqueous solution containing alcohol.

In some embodiments, the aforementioned composition may be an edible composition for non-medical purposes, and this edible composition includes at least a specific content of queen plum extract. In some embodiments, the edible composition may be a food product or a food additive. That is, the queen plum extract of any of the aforementioned embodiments can be added by a well-known method during preparation of food materials to prepare food products, or the queen plum extract of any of the aforementioned embodiments is added directly in the preparation process of food products. Here, the food products may be formulated with edible materials into products for human or animal consumption. In some embodiments, the edible composition may further include a food body, or may further include a food body and food additives.

In some embodiments, the food products may be, but are not limited to, beverages, fermented foods, bakery products, health foods for non-medical purposes, dietary supplements for non-medical purposes, or the like.

Here, the following experimental data were calculated using an STDEV formula for a standard deviation, and whether there is a significant statistical difference between two sample populations is analyzed with a single-tailed student t-test.

Example 1: Preparation of Test Sample 1-1. Materials and Instruments:

Here, the *Prunus salicina* produced in Queensland, Australia was used, and water was used as a solvent.

1-2. Preparation Step:

The water was heated to 85° C., then complete fruit of the *Prunus salicina* was added in a weight ratio of 1:5 of the *Prunus salicina* to the water, and the *Prunus salicina* was soaked in the water at 85° C. for 1 h to obtain an initial extraction solution. Here, Degrees Brix of the initial extraction solution was 7.5° Bx or above. Subsequently, the obtained initial extraction solution was sieved through a 400-mesh sieve and a filtrate was obtained as the queen plum extract.

Example 2: Test of Inhibition of Blue Light Damage

Here, changes in reactive oxygen species (ROS) content in human skin fibroblasts CCD-966sk treated with the queen plum extract in Example 1 were determined using a fluorescent probe DCFH-DA combined with a flow cytometer. The more the reactive oxygen species, the more damage by blue light.

2-1. Materials and Instruments:

Cell line: Human skin fibroblasts CCD-966sk (BCRC No. 60153), hereinafter referred to as skin fibroblasts.

Cell medium: An Earle's balanced salt type of minimum essential medium (MEM) additionally supplemented with 0.1 M non-essential amino acid, 1.5 g/L sodium bicarbonate, 0.1 M pyruvate, and 10% fetal bovine serum (purchased from Gibco®).

Buffer salt solution (PBS solution): purchased from Gibco®, with a product number of 14200-75.

Reactive oxygen species dye: Fluorescent dye DCFH-DA (purchased from Sigma®/SI-D6883-50 MG). DCFH-DA was formulated with dimethyl sulfoxide (DMSO) into a reactive oxygen species dye with a concentration of 5 mg/ml, which could be used for dyeing reactive oxygen species.

Flow cytometer: Purchased from the BD Pharmingen™, with a model of BDTM Accuri C6 Plus.

Trypsin: 10× Trypsin-EDTA (purchased from Gibco®, with a product number of 15400-054).

2-2. Test Step:

The skin fibroblasts were inoculated into 6-well culture plate containing 2 mL of cell medium per well at a density of $2\times10^5$ per well, and cultured in an incubator with a $CO_2$ concentration of 5% and a temperature of 37° C. for 24 h.

The medium in each well of the culture plate was replaced with 2 mL of test medium, and then the culture plate was placed in an environment with 5% $CO_2$ and a temperature of 37° C., and cultured for 1 h. The test medium in an experimental group 01 is a cell medium containing 0.03125% (m/v) of queen plum extract prepared in Example 1, and the test medium in an experimental group 02 is a cell medium containing 0.0625% (m/v) of queen plum extract prepared in Example 1. The test media in a blank group and a control group were each a pure cell medium (i.e., without the queen plum extract).

Afterwards, 5 μg/mL of reactive oxygen species dye was added into each well and allowed to react and stain for 15 min.

After the staining was completed, the experimental group 01, the experimental group 02 and the control group were placed in a blue light irradiation apparatus, and the cells were irradiated with blue light of 400 to 500 nm for 1 h, while the blank group was not irradiated with blue light.

After 1 h, the cells in each group were washed twice with a PBS solution, then 200 μL trypsin was added, and a reaction was carried out in the absence of light for 5 min.

The cells in each group after the reaction were transferred into a 15 ml test tube and the test tube was centrifuged at 400×g for 10 min. After supernatant in the test tube was removed, the cells in the test tube were washed once with the PBS solution. Subsequently, each group was centrifuged again at 400×g for 10 min. After the centrifugation, the supernatant in each group was removed, and then, 1 ml of PBS solution was added to each group to suspend the cells in the test tube to obtain a cell suspension.

Finally, the cell suspension in each group was detected by the flow cytometer for fluorescent signals (corresponding to reactive oxygen species content in the cells) at an excitation wavelength of 450 to 490 nm and a radiation wavelength of 510 to 550 nm, and based on this, the proportion of the number of cells with highly expressed reactive oxygen species in the cells to the number of primary cells was calculated and used as the relative production of the reactive oxygen species (ROS) of the cells, as shown in FIG. 1.

2-3. Test Result:

In FIG. 1, "#" represents a statistical difference relative to the blank group, and the greater the number of "#", the more significant the difference. "#" represents that p value is less than 0.05, "##" represents that p value is less than 0.01, and "###" represents that p value is less than 0.001. "*" represents a statistical difference relative to the control group, and the greater the number of "*", the more significant the difference. "*" represents that p value is less than 0.05, "" represents that p value is less than 0.01, and "*" represents that p value is less than 0.001.

See FIG. 1, the skin fibroblasts in the blank group were not irradiated with the blue light, that is, they were under normal physiological metabolism conditions. Here, the fluorescent signal in the blank group was set to 100% of the relative production of the reactive oxygen species, and the fluorescent signal in each group was converted into the relative production of the reactive oxygen species of a corresponding proportion. After the skin fibroblasts in the control group were irradiated with the blue light for 1 h, the relative production of the reactive oxygen species was as high as 72211.11%. It can be seen that the blue light will seriously damage human skin, causing the skin fibroblast to produce a large amount of reactive oxygen species, which can cause great damage to the human skin.

See FIG. 1 further. Compared with that of the control group, the relative production of the reactive oxygen species of the skin fibroblasts in the experimental group 01 treated with the queen plum extract with a concentration of 0.03125% was significantly reduced to 869.44%. The relative production of the reactive oxygen species of the human skin fibroblasts in the experimental group 02 treated with the queen plum extract with a concentration of 0.0625% was significantly reduced to 580.56%. That is, after 1 h of blue light irradiation, the relative production of the reactive oxygen species in either the experimental group 01 or the experimental group 02 was significantly reduced compared with that of the control group. This experimental result shows that the queen plum extract can significantly inhibit the skin damage caused by blue light, can promote the antioxidant capacity of the skin, and can reduce the number of ROS produced by blue light irradiation on the skin.

Example 3: Test of Promotion of Collagen Production 3-1. Materials and Instruments:

Cell line: Human skin fibroblasts CCD-966sk (ATCC® No. CRL-1881), hereinafter referred to as skin fibroblasts.

Cell medium: A minimum essential medium (hereinafter referred to MEM) (Gibco®, with a product number of 11095080) supplemented with 10% of fetal bovine serum (FBS; Gibco®, with a product number of 10437-028), 1% of penicillin-streptomycin (Gibco®, with a product number of 15140122) and 1 mM of sodium pyruvate (Gibco®, with a product number of 11360-070).

Test kit for collagen type I (Elisa Kit, Cloud-clone, SEA571Hu, 96 tests/box, for Collagen Type I (COL1) (USCN)).

Enzyme immunoassay analyzer (ELISA reader brand BioTek).

3-2. Test Flow:

Firstly, the skin fibroblasts were implanted into a 24-well cell culture plate at a density of $2\times10^4$ skin fibroblasts, and 500 μL of cell culture fluid was added, and cultured in a carbon dioxide incubator at 37° C. for 24 h. After being attached to the bottom of the cell culture plate, the fibroblasts were washed once with 1× DPBS.

The skin fibroblasts were divided into an experimental group and a blank group. 500 L of test medium was added into each well, and then cultured at 37° C. for 48 h.

The test medium in an experimental group 01 is a cell medium containing 0.03125% (m/v) of queen plum extract prepared in Example 1, and the test medium in an experimental group 02 is a cell medium containing 0.0625% (m/v) of queen plum extract prepared in Example 1. The test media in the blank group were each a pure cell medium (i.e., without the queen plum extract).

Samples to be tested in each of the above-mentioned groups were collected and treated according to the specifications of the test kit for collagen to form a solution to be tested in each group. Subsequently, an absorbance value of the solution at 450 nm in each group was measured by a spectrophotometer. The test results are as shown in FIG. 2.

3-3. Test Result:

Here, displayed collagen secretion was presented in relative rate, where a standard deviation was calculated by using the STDEV formula of Excel software, whether there was a statistically significant difference or not was analyzed with a single-tailed student t-test in an Excel software. In the figure, "*" represents that the p value is less than 0.05, and "**" represents that the p value is less than 0.01. The more the "*", the more significant the statistical differences.

Figure 2:
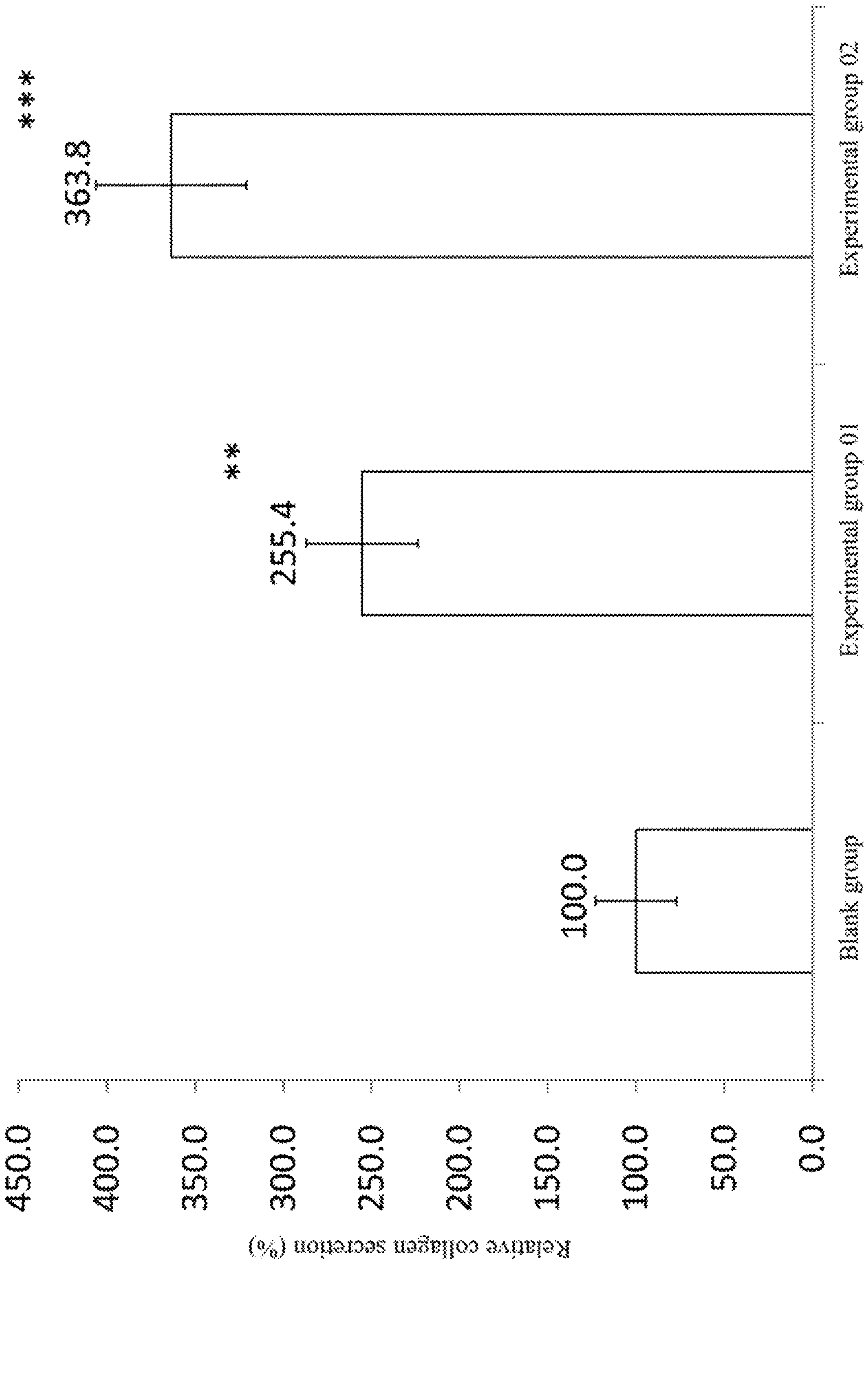
FIG. 2 is a bar chart showing the relative collagen content.

See FIG. 2. Values in the blank group were regarded as 100%. Compared with that of the blank group, the relative secretion of collagen in the experimental group 01 was 255.4%, and the relative secretion of collagen in the experimental group 02 was 363.8%, showing a statistically significant difference. It can be seen that the queen plum extract can significantly promote the secretion of a large amount of collagen by the human skin fibroblasts, and can significantly increase the secretion by more than 2.5 times that of normal secretion. It can be seen from that the queen plum extract can effectively secrete the collagen in the human skin fibroblasts, thereby reducing skin sagging.

Example 4: Cell Gene Expression Level Test

Here, detected genes include a COL1A1 gene (Gene ID: 1277), an MMP9 gene (Gene ID: 4318), a TIMP1 gene (Gene ID: 7076), an LOX gene (Gene ID: 4015), and an HAS2 gene (Gene ID: 3037).

The COL1A1 gene is a member of collagen type I (fibrogenic collagen). MMP9 is a collagen degrading enzyme. Therefore, inhibiting the expression of the MMP9 gene can prevent the loss of collagen. TIMP1 is an enzyme inhibiting collagen decomposition, working by forming a one-to-one complex with a target metalloproteinases (such as a collagenase), and inactivating the collagenase by binding to its catalytic zinc cofactor. LOX (Lysyl oxidase) is responsible for translation of peptidyl lysine residues in fibrous collagen and elastin precursors, so that the collagen and the elastin are cross-linked to stabilize the integrity and elasticity between collagen fibers and mature elastin, thereby maintaining the extracellular matrix. HAS2 is a hyaluronan synthase.

4-1. Materials and Instruments:

Cell line: Human skin fibroblasts CCD-966sk, taken from the Bioresources Collection and Research Center (BCRC; Cat. 60153), hereinafter referred to as skin fibroblasts.

Cell medium: A minimum essential medium (hereinafter referred to MEM) (Gibco®, with a product number of 11095080) supplemented with 10% of fetal bovine serum (FBS; Gibco®, with a product number of 10437-028), 1% of penicillin-streptomycin (Gibco®, with a product number of 15140122) and 1 mM of sodium pyruvate (Gibco®, with a product number of 11360-070).

p value is less than 0.05 in comparison with that of the blank group, '' represents that its p value is less than 0.01 in comparison with that of the blank group, and '*' represents that its p value is less than 0.001 in comparison with that of the blank group.

TABLE 1

| Target gene | Primer name | Sequence number | Sequence | Primer length |
|---|---|---|---|---|
| HAS2 | HAS2-F | SEQ ID NO: 1 | AAGAACAACTTCCACGAAAAGGG | 23 |
| | HAS2-R | SEQ ID NO: 2 | GGCTGGGTCAAGCATAGTGT | 20 |
| LOX | LOX-F | SEQ ID NO: 3 | CGGCGGAGGAAAACTGTCT | 19 |
| | LOX-R | SEQ ID NO: 4 | TCGGCTGGGTAAGAAATCTGA | 21 |
| TIMP1 | TIMP1-F | SEQ ID NO: 5 | AGAGTGTCTGCGGATACTTCC | 21 |
| | TIMP1-R | SEQ ID NO: 6 | CCAACAGTGTAGGTCTTGGTG | 21 |
| MMP9 | MMP9-F | SEQ ID NO: 7 | TGTACCGCTATGGTTACACTCG | 22 |
| | MMP9-R | SEQ ID NO: 8 | GGCAGGGACAGTTGCTTCT | 19 |
| COL1A1 | COL1A1-F | SEQ ID NO: 9 | ATCAACCGGAGGAATTTCCGT | 21 |
| | COL1A1-R | SEQ ID NO: 10 | CACCAGGACGACCAGGTTTTC | 21 |

4-2. Test Flow:

Firstly, $1\times10^5$ skin fibroblasts were taken and placed in a 6-well cell culture plate containing 2 mL of cell medium per well, then the culture plate was placed at 37° C. and cultured for 24 h.

The skin fibroblasts were divided into an experimental group and a blank group. The cell medium in each group was removed and replaced with 2 mL test medium per well, then the culture plate was placed at 37° C. and cultured for 24 h. The test medium in the experimental group was a cell medium containing 0.0625% (m/v) of queen plum extract prepared in Example 1. The test media in the blank group were each a pure cell medium (i.e., without the queen plum extract).

The skin fibroblasts in each group were collected and RNA in each group was extracted using an RNA extraction reagent kit (purchased from Geneaid, Taiwan, Lot No. FC24015-G). Subsequently, 1000 ng of RNA was taken from each group as a template, and was reversely transcribed into corresponding cDNA using SuperScript® III reverse transcriptase (purchased from Invitrogene®, USA, code 18080-051). Then a quantitative real-time reverse transcription polymerase chain reaction was carried out on the cDNA in each group by ABI StepOnePlus™ Real-Time PCR system (Thermo Fisher Scientific®, USA), KAPA SYBR FAST (purchased from Sigma®, USA, No. 38220000000) and primers in Table 1 (SEQ ID NO: 1 to SEQ ID NO: 10) to observe the expression level of related genes in skin fibroblasts. Instrument set conditions for the quantitative real-time reverse transcription polymerase chain reaction were as follows: a reaction was carried out at 95° C. for 20 s, followed by a reaction at 95° C. for 3 s, and a reaction at 60° C. for 30 s, which was repeated for 40 cycles, and gene quantification was performed using a 2-ΔCt method. Here, the quantitative real-time reverse transcription polymerase chain reaction using the cDNA could indirectly quantify the mRNA expression level of a gene, and then, the expression level of a protein coded by the gene was inferred.

In FIG. 3 to FIG. 7, "*" represents a statistical difference relative to the blank group, and the greater the number of "*", the more significant the difference. '*' represents that its In Table 1, F is a forward prime and R is a reverse prime.

Figure 3:
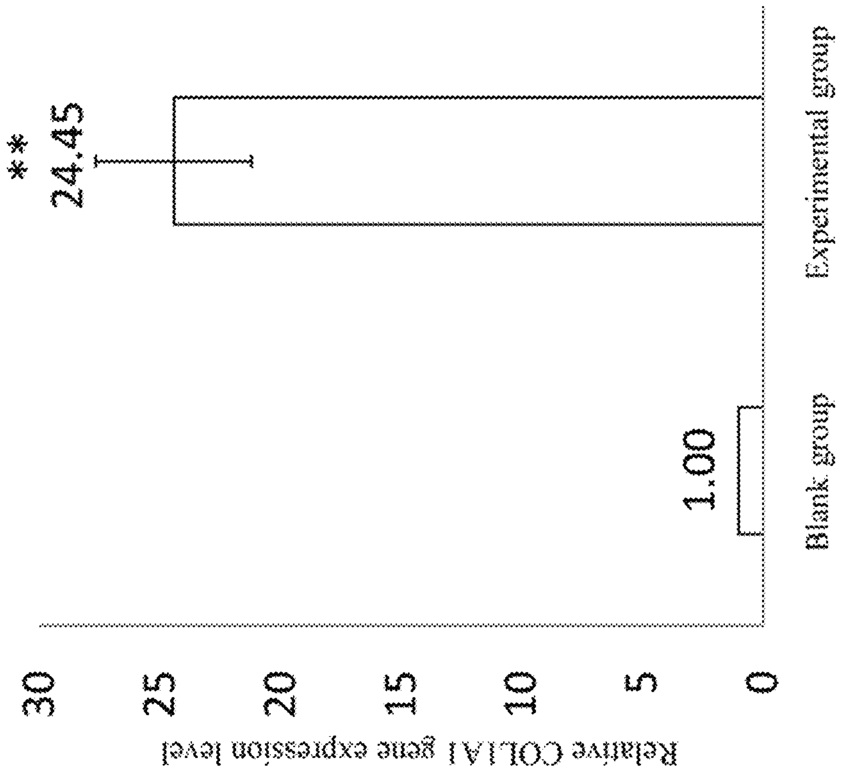
FIG. 3 is a bar chart showing the expression level of COL1A1 gene.

4-3. Test Result:

See FIG. 3. The relative expression rate of the COL1A1 gene in the blank group was regarded as 1. Compared with that of the blank group, the relative expression rate of the COL1A1 gene in the experimental group was 24.45. It can be seen that the expression level of the COL1A1 gene treated with the queen plum extract in the experimental group is significantly increased, indicating that the queen plum extract can promote the production of collagen type I by cells themselves.

Figure 4:
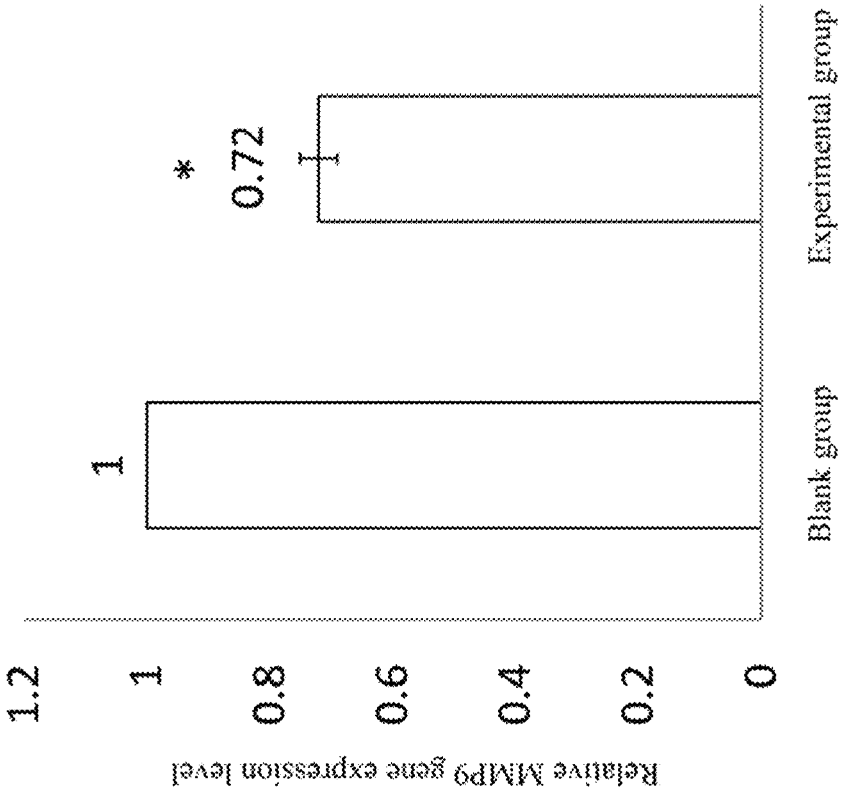
FIG. 4 is a bar chart showing the expression level of MMP9 gene.

Continue to see FIG. 4. The relative expression rate of the MMP9 gene in the blank group was regarded as 1. Compared with that of the blank group, the relative expression rate of the MMP9 gene in the experimental group was 0.72. It can be seen that the expression level of the MMP9 gene treated with the queen plum extract in the experimental group is significantly decreased, indicating that the queen plum extract can inhibit the number of the collagen degrading enzymes, thereby avoiding the loss of the collagen.

Figure 5:
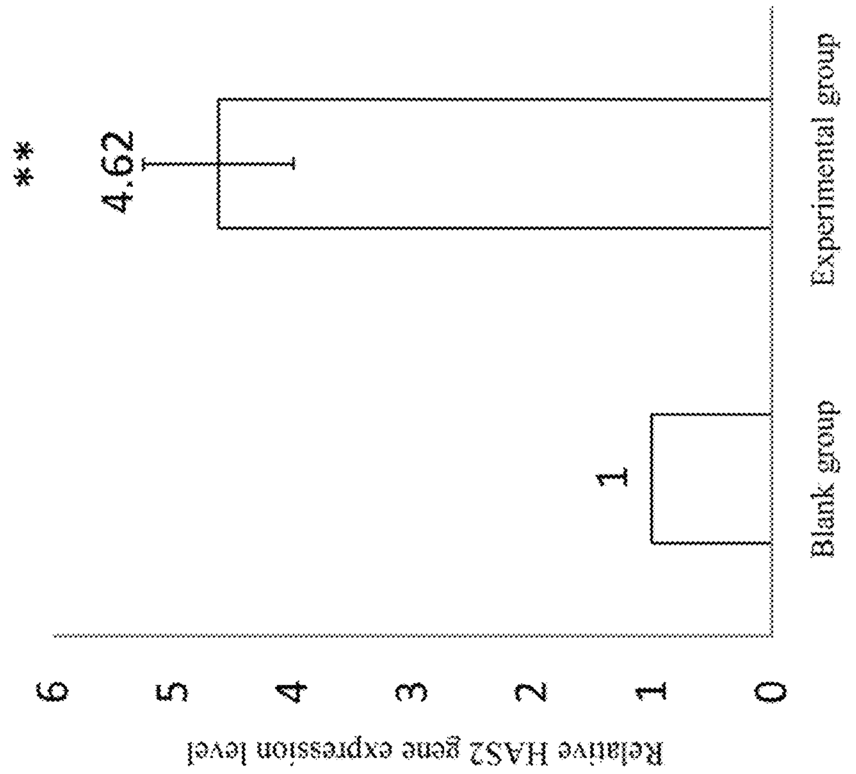
FIG. 5 is a bar chart showing the expression level of HAS2 gene.

Continue to see FIG. 5. The relative expression rate of the HAS2 gene in the blank group was regarded as 1. Compared with that of the blank group, the relative expression rate of the HAS2 gene in the experimental group was 4.62. It can be seen that the expression level of the HAS2 gene treated with the queen plum extract in the experimental group is significantly increased, indicating that the queen plum extract can promote the content of hyaluronan synthase, thereby increasing hyaluronan content in skin, maintaining skin moisture, and avoiding skin sagging.

Figure 6:
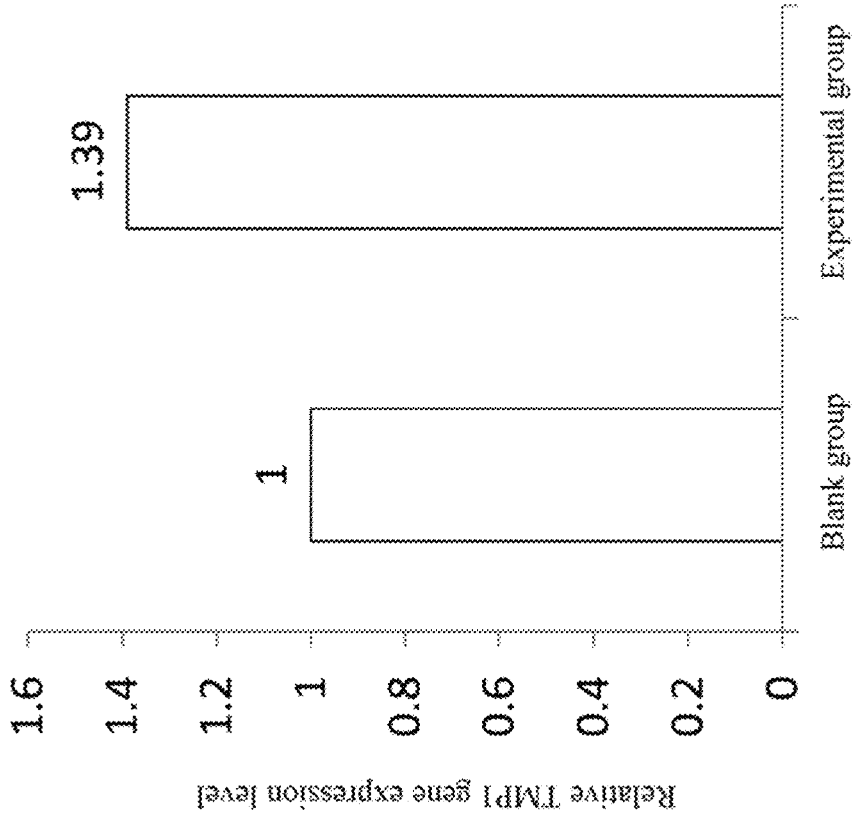
FIG. 6 is a bar chart showing the expression level of TIMP1 gene.

Continue to see FIG. 6. The relative expression rate of the TIMP1 gene in the blank group was regarded as 1. Compared with that of the blank group, the relative expression rate of the TIMP1 gene in the experimental group was 1.39. It can be seen that the expression level of the TIMP1 gene treated with the queen plum extract in the experimental group is significantly increased, indicating that the queen plum extract can inhibit the collagen degrading enzymes, thereby avoiding the loss of the collagen.

Figure 7:
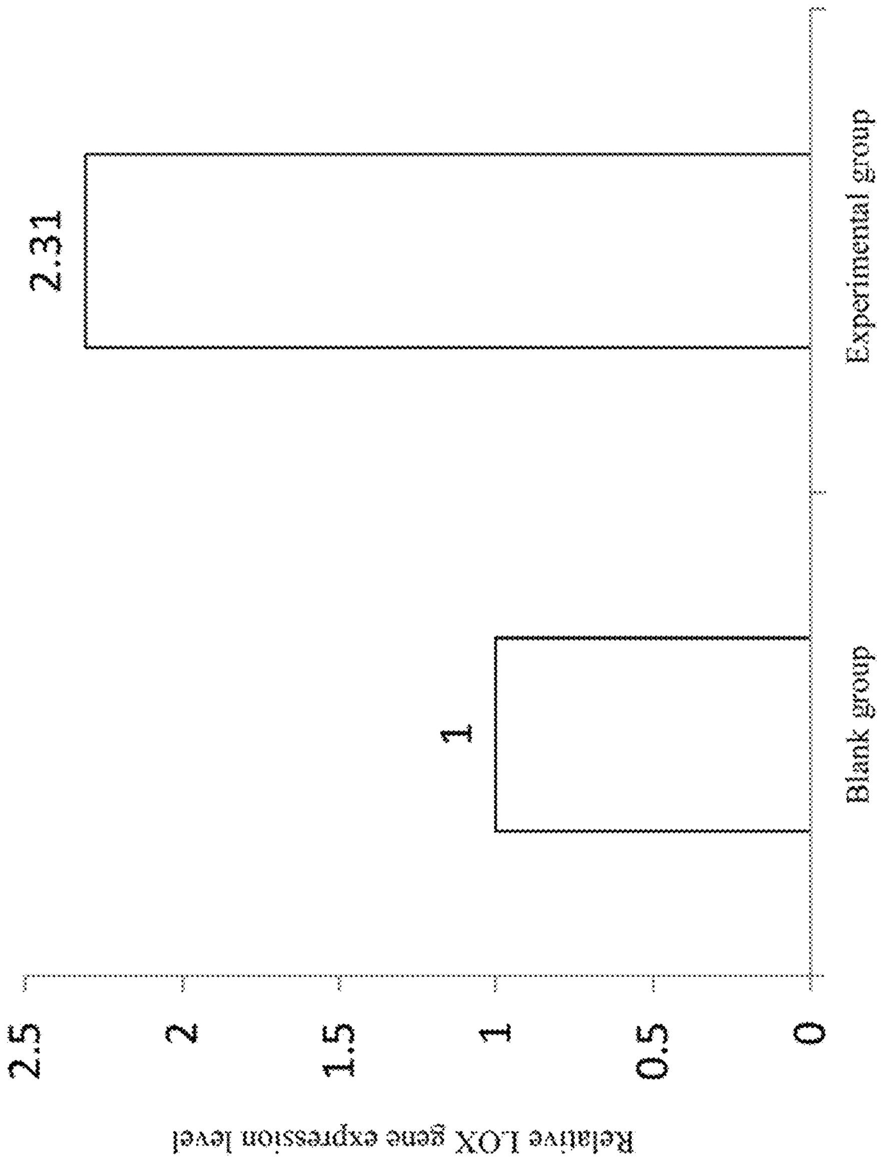
FIG. 7 is a bar chart showing the expression level of LOX gene.

Continue to see FIG. 7. The relative expression rate of the LOX gene in the blank group was regarded as 1. Compared with that of the blank group, the relative expression rate of the LOX gene treated with the queen plum extract in the experimental group was 2.31. It can be seen that the expression level of the LOX gene in the experimental group is significantly increased, indicating that the queen plum extract can stabilize the integrity between the collagen fibers and the mature elastin, thereby maintaining the extracellular matrix.

Example 5: Human Experiment

Sample: The queen plum extract prepared in Example 1 was used.

Subject: 13 subjects. All the subjects were adults aged above 20 and under 65 years old. Generally, the reference range of ferritin content in blood of a normal female in medicine was between 11 ng/dL and 306.8 ng/dL, and the reference range of ferritin content in blood of a normal male was between 23.9 ng/dL and 336.2 ng/dL. If less than 11.5 ng/dL, the ferritin content in blood was judged as low. The 3 females of the subjects in this experiment had low ferritin content (<11 ng/dL) in their blood.

5-1. Test Items:

Items include ferritin content in blood, skin sagging degree, and amount of skin porphyrin.

Regarding the ferritin content in blood, blood was taken as a sample, and the entrusted inspection institution was the Lezen Laboratory Center.

Regarding the skin sagging degree, the facial skin of the same subject before and after taking the sample was detected using a skin elasticity detection probe Cutometer® MPA580 (C+K Multi Probe Adapter System, Germany) purchased from the Courage+Khazaka electronic in Germany. The test principle was based on principles of suction and stretching. Negative pressure was generated on the surface of tested skin to suck the skin into a test probe. The depth of the skin sucked into the probe was detected with an optical test system, and the skin sagging degree was analyzed and calculated with software. After the measurement, the skin sagging degree at week 0 was taken as a benchmark (that is, the relative expression rate of the skin sagging degree at week 0 was 100%), the skin sagging level (%) at weeks 2 and 4 was calculated.

Based on the fact that *Bacillus acnes* would secrete porphyrin during growth, the porphyrin would produce fluorescence under UV irradiation. In this test, after the facial skin was photographed with UV light, the skin porphyrin content was detected using VISIA® Complexion Analysis System (Canfield scientific, USA). The higher the measurement value, the more vigorous the growth of *Bacillus acnes*, and the more prone to acnes. Here, after the measurement of the porphyrin, the amount of the porphyrin at week 0 was taken as a benchmark (that is, the relative amount of the porphyrin in the skin at week 0 was 100%), the relative content (%) of the porphyrin in the skin at weeks 2 and 4 was calculated by conversion.

5-2. Test Flow:

The 13 subjects were allowed to take 0.5 g of queen plum extract daily for four weeks. Measurements were performed with the above-mentioned devices or methods before the start of intake (i.e., week 0), two weeks after intake (i.e., week 2) and four weeks after intake (i.e., week 4).

Figure 8:
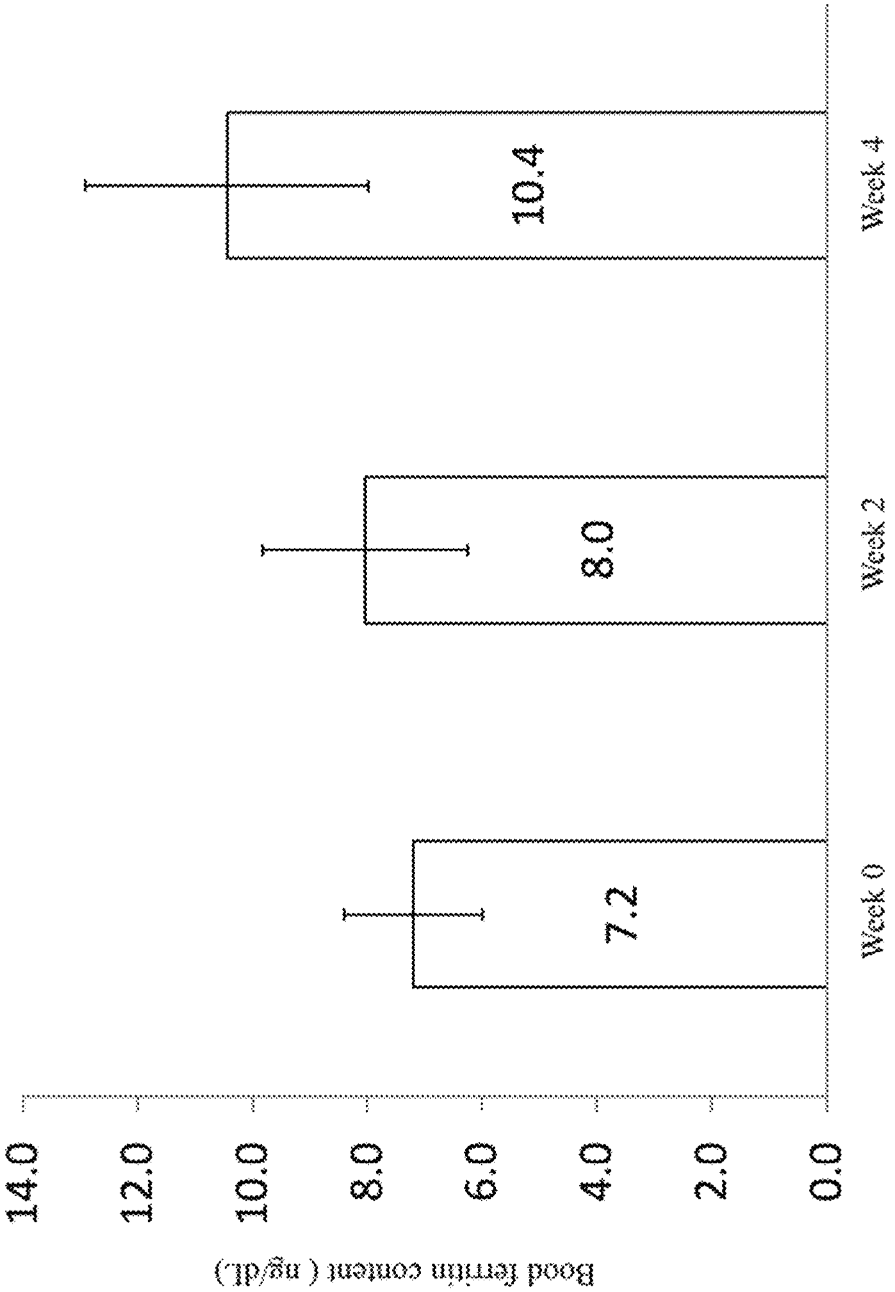
FIG. 8 is bar chart showing the blood ferritin content of human subjects.

5-3. Test Result:

See FIG. 8. The 3 (female) subjects, with low ferritin content in blood, of the subjects were observed. After two weeks of daily intake of 0.5 g of queen plum extract, the average ferritin content in blood of the 3 subjects with the low ferritin content in blood was increased from 7.2 μg/dL (week 0) to 8.0 μg/dL (week 2) where the daily routine was maintained. After another two weeks of continuous daily intake of 0.5 g of queen plum extract, the average ferritin content in blood was increased to 10.4 μg/dL (week 4) where the daily routine was maintained. That is, supplementing the queen plum extract can increase the ferritin content in blood of the subject with the low ferritin content in blood to a near-normal level.

Figure 9:
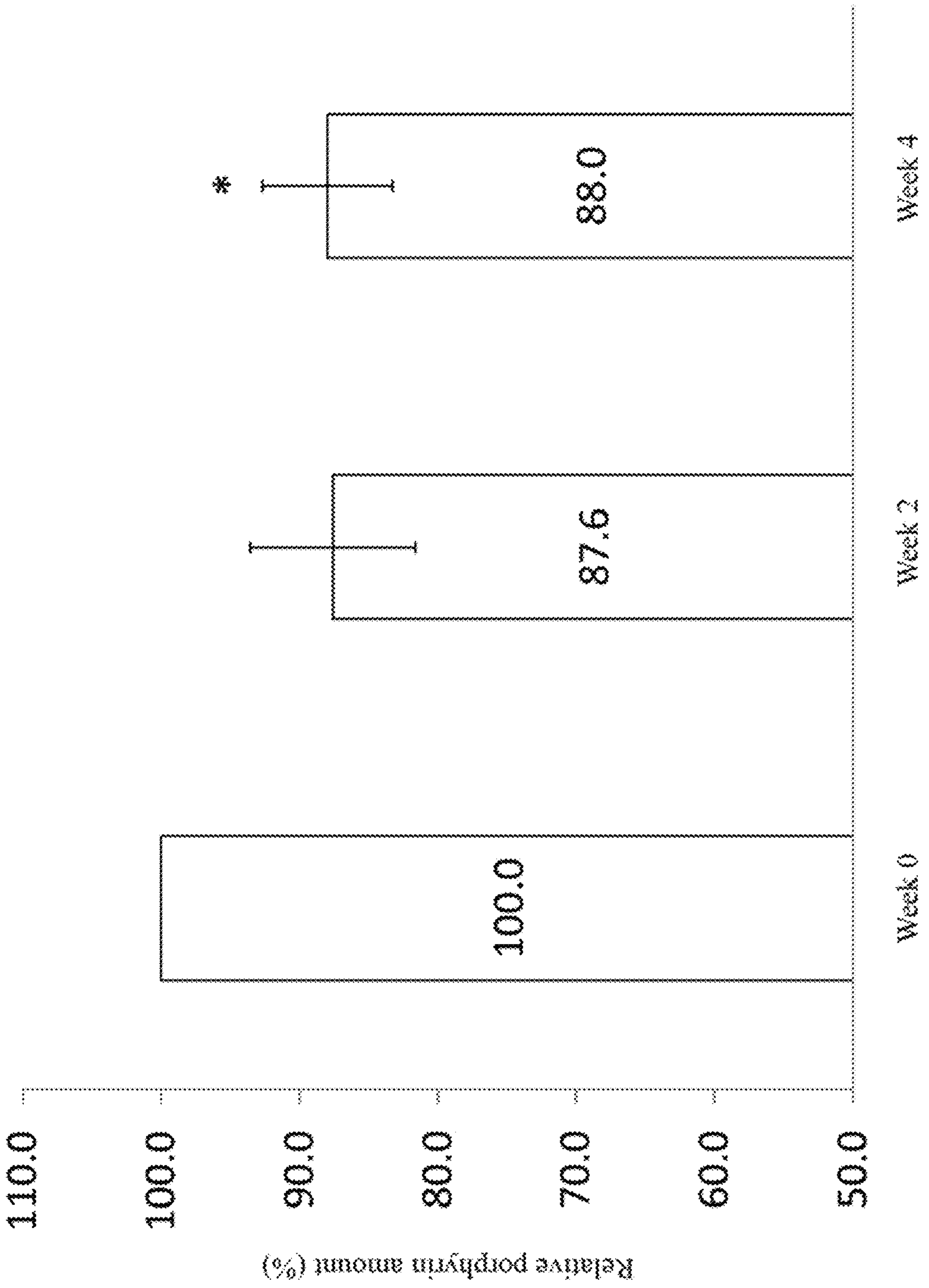
FIG. 9 is a bar chart showing the relative porphyrin content of human subjects.

See FIG. 9. After two weeks of daily intake of 0.5 g of queen plum extract, the average skin porphyrin amount of 13 subjects was decreased from 100% (week 0) to 87.6% (week 2) where the daily routine was maintained. After another two weeks of continuous daily intake of 0.5 g of queen plum extract, the average skin porphyrin level was increased to 88.0% (week 4) where the daily routine was maintained. That is, supplementing the queen plum extract can significantly reduce the amount of porphyrin in the facial skin within two weeks, while continuous supplementation can maintain the amount of porphyrin without increasing again, thereby reducing the probability of incidence of acnes.

Figure 10:
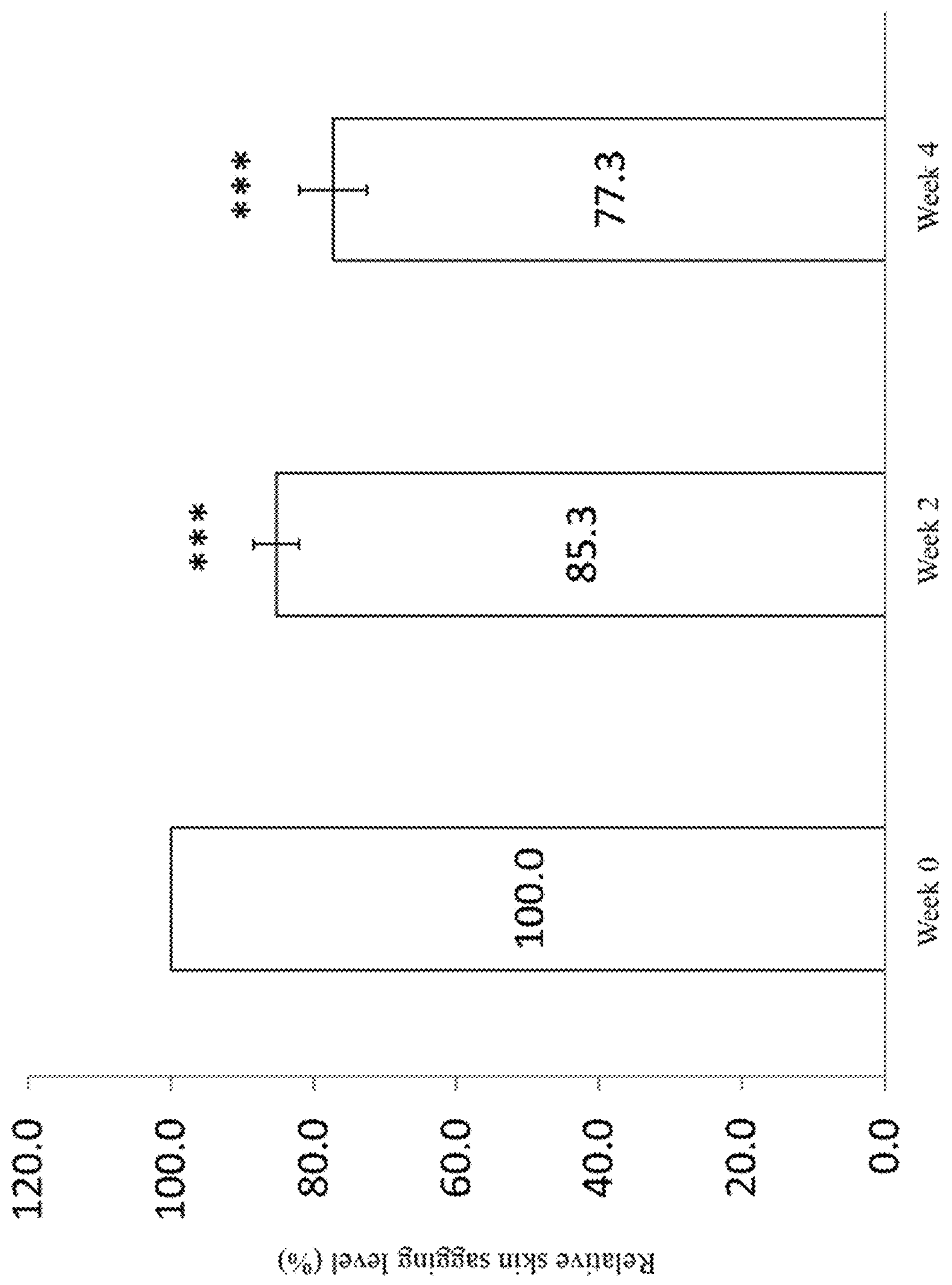
FIG. 10 is a bar chart showing the relative skin sagging level of human subjects.

See FIG. 10. After two weeks of daily intake of 0.5 g of queen plum extract, the average skin sagging level of 13 subjects was decreased from 100% (week 0) to 85.3% (week 2) where the daily routine was maintained. After another two weeks of continuous daily intake of 0.5 g of queen plum extract, the average skin sagging level was increased to 77.3% (week 4) where the daily routine was maintained. That is, supplementing the queen plum extract significantly reduces the skin sagging level of the facial skin, and continuous supplementation achieves a better effect.

Example 6: Fingerprint HPLC Test of Queen Plum Extract

Here, bioactive substances in the queen plum extract prepared in Example 1 were quantitatively and qualitatively analyzed using high performance liquid chromatography (HPLC).

Solvents used in this test were methanol and water, and 0.1% formic acid was added to each of the methanol and the water. The flow rate was set as 1 ml/min, and the elution conditions were set as 2:98 of methanol to water at 0 min, 2:98 of methanol to water at 10 min, 70:30 of methanol to water at 40 min, 100:0 of methanol to water at 50 min and 100:0 of methanol to water at 60 min. Here, the sample concentration was 50 mg/ml, the injection volume was 10 μL, and the column temperature during the experiment was 40° C.

Figure 11:
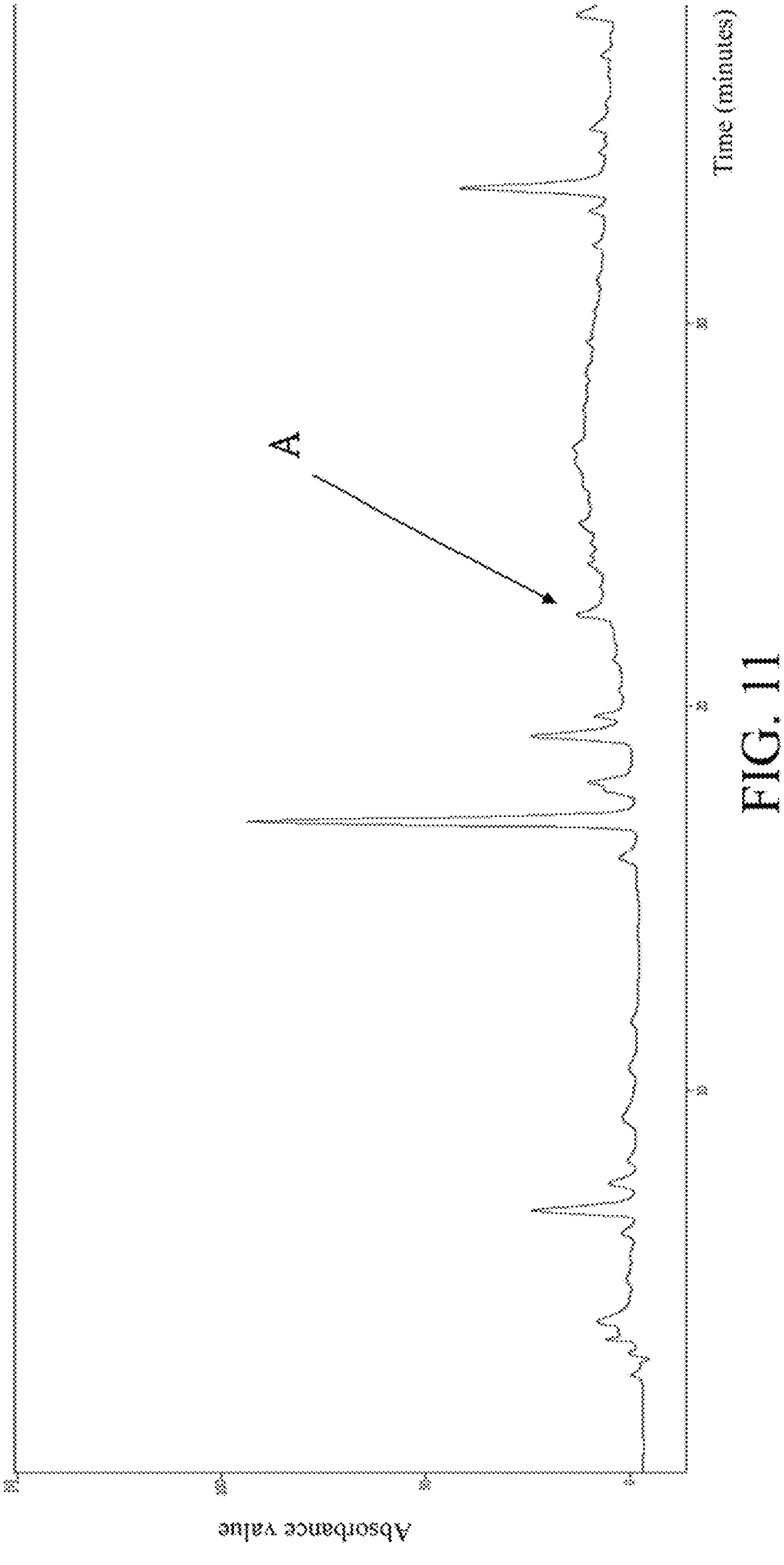
FIG. 11 is a liquid chromatography spectrum of the queen plum extract in accordance with an embodiment of the present disclosure.

See FIG. 11. The wave peak of bioactive substance A, which was separated out at around 22.7 min, was confirmed to be cumoricanhydride (Coumaroyl-β-glucosyl-(1→2)-β-glucosyl-(1→2)-β-glucoside) after analysis and comparison.

Here, the bioactive substance A has a chemical structure as shown below.

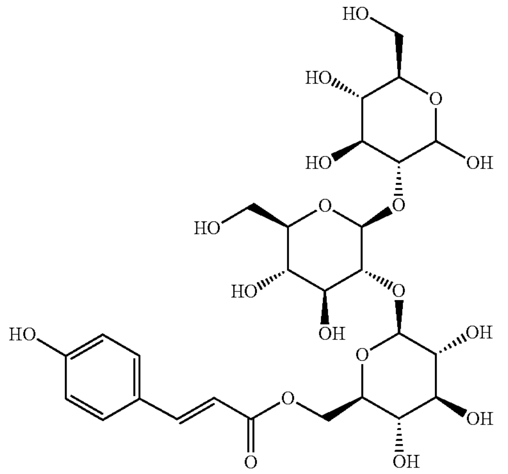 [SMILES: O=C(/C=C/c1ccc(O)cc1)OC[C@H]1O[C@@H](O[C@H]2[C@H](O[C@H]3C(O)O[C@H](CO)[C@@H](O)[C@@H]3O)O[C@H](CO)[C@@H](O)[C@@H]2O)[C@H](O)[C@@H](O)[C@@H]1O]

Example 7: Test of Cumoricanhydride to Increase Cell Iron Content

This test was conducted using intestinal epithelial cells to measure the iron content within intestinal cells to test whether the absorption capacity of iron by intestines was improved or not.

7-1. Materials and Instruments:

Cell line: A human colon cell C2BBel (ATCC® CRL-2102TM) was used.

C2BBel medium: prepared from 90% DMEM medium (Dulbecco's Modified Eagle Medium, Gibco®) supplemented with 10% of fetal bovine serum (Gibco®), 1% of antibiotic-antimycotic (Gibco®), and 0.01 mg/ml transferrin.

Iron-free medium: prepared from a minimum essential medium (Gibco®) supplemented with 10 mmol/L PIPES (firstly, NaOH was filtered to prepare 150 mg/mL solution, then 1 mL to 50 mL medium was filtered and taken), 4 mg/L hydrocortisone (10 μL of 20 mg/ml hydrocortisone was taken and added to 50 mL medium), and 5 μg Se/L sodium selenite (1 μL of 250 μg/ml sodium selenite was taken and added to 50 mL medium), 34 μg/L triiodothyronine (0.17 μL of 10 mg/mL triiodothyronine was taken and added to 50 mL medium), 5 mg/L insulin (25 μL of 10 mg/mL insulin was taken and added to 50 mL medium), 20 μg/L epidermal growth factor (EGF) (10 μL of 100 mg/mL EGF was taken and added to 50 mL medium) and 1× antibiotic-antimycotic (Gibco®).

An ELISA kit for human ferritin FTL was purchased from Abcam. (Protein concentration was measured using braford assay)

RIPA buffer (brand: Thermo, model: 89900).

7-2. Test Flow:

Firstly, initial cultivation of the cells was carried out. $2\times10^4$ cells and 500 μL of C2BBel medium were inoculated into each well of a 24-well plate, and cultured at 37° C. for 14 d, and the medium was replaced every 3 d.

The C2BBel medium was removed, the cells were washed, and then the washed cells were cultivated in the iron-free medium for 2 d.

The cells cultured in the iron-free medium for 2 d were divided into a blank group and an experimental group, where the iron-free medium in the blank group was replaced with a fresh iron-free medium only, while the iron-free medium in the experimental group was replaced with a fresh iron-free medium, and 0.0625% (m/v) of queen plum extract prepared in Example 1 was added.

Additional 10 μmol/mL of $FeSO_4$ was added to each group to serve as an iron source, and cultivated for 24 h. Subsequently, the cells in each group were collected, and then, 200 mL of RIPA buffer was added and stored at −20° C. Finally, the ferritin content in the cells in each group was measured using the ELISA kit for human ferritin FTL.

Figure 12:
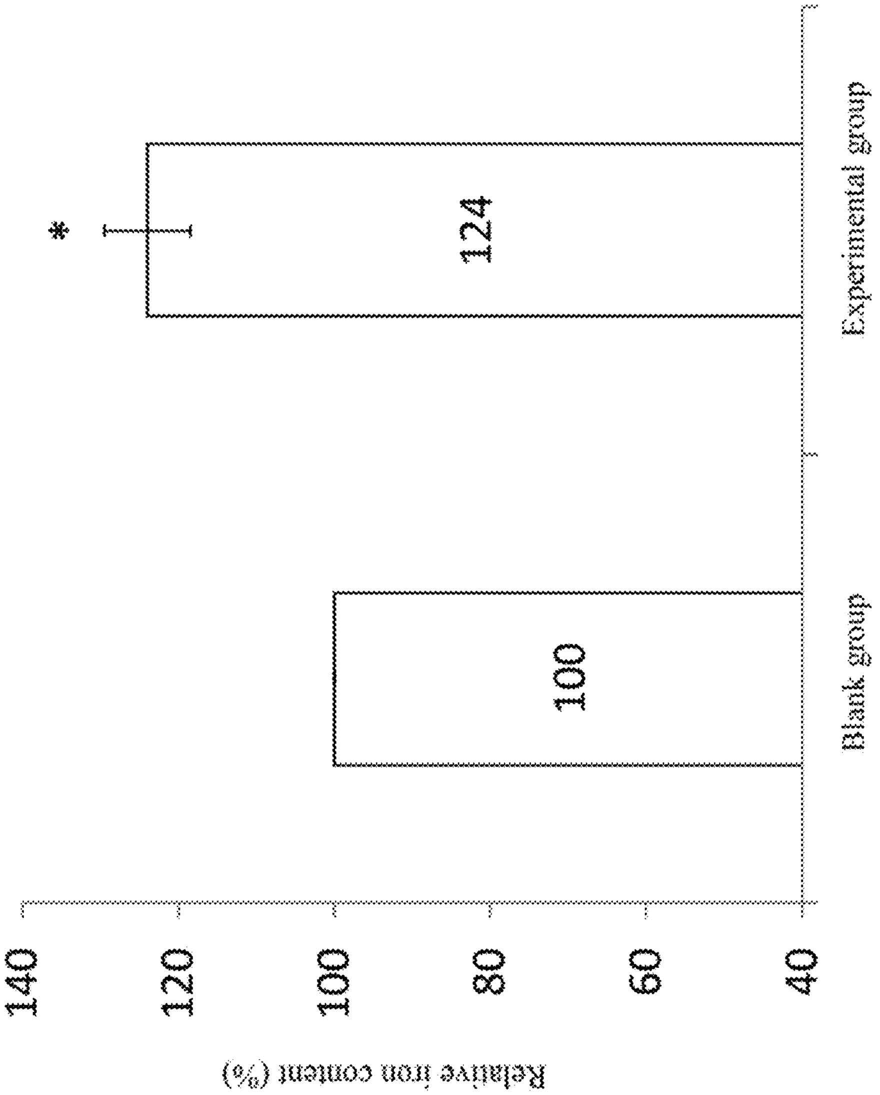
FIG. 12 is a bar chart showing the effect of coumaric acid in increasing cell iron content.

7-3. Test Result:

In FIG. 12, "*" represents a statistical difference relative to the blank group, and the greater the number of "*", the more significant the difference. '*' represents that its p value is less than 0.05 in comparison with that of the blank group, '' represents that its p value is less than 0.01 in comparison with that of the control group, and '*' represents that its p value is less than 0.001 in comparison with that of the control group.

See FIG. 12. It can be seen that, based on the iron content of the blank group being 100%, the ferritin content in the human colon cells treated with the queen plum extract in the experimental group was significantly increased by 124%. That is, the queen plum extract has the effect of promoting absorption of iron by the intestines.

In summary, the queen plum extract of any embodiment can be used for preparing the composition for inhibiting skin damage caused by blue light, reducing skin sagging, reducing skin porphyrin content, or increasing ferritin content. In some embodiments, the queen plum extract has at least one of the following effects: promoting antioxidant capacity of the skin, reducing the amount of ROS produced by the skin in response to blue light irradiation, promoting moisture retention capacity of the skin, improving skin elasticity, improving collagen content, enhancing expression of COL1A1 gene and/or TIMP1 gene, inhibiting expression of MMP9 gene, promoting hyaluronan synthesis, promoting expression of HAS2 gene, maintaining the extracellular matrix, enhancing expression of LOX gene, and reducing incidence of acnes.

Although the present invention has been described in considerable detail with reference to certain preferred embodiments thereof, the disclosure is not for limiting the scope of the invention. Persons having ordinary skill in the art may make various modifications and changes without departing from the scope and spirit of the invention. Therefore, the scope of the appended claims should not be limited to the description of the preferred embodiments described above.

What is claimed is:

1. A method for reducing skin porphyrin content and incidence of acnes in a subject in need thereof, comprising: orally administering to the subject an effective dose of queen plum extract, wherein the queen plum extract is obtained by extracting whole fruit of *Prunus salicina* by water at 85° C. for 1 h.

2. A method for increasing ferritin content within intestinal cells in a subject in need thereof, comprising: administering to the subject an effective dose of queen plum extract, wherein the queen plum extract is obtained by extracting whole fruit of *Prunus salicina* by water.

3. The method according to claim 2, wherein the queen plum extract comprises coumaroyl-β-glucosyl-(1→2)-β-glucosyl-(1→2)-β-glucoside.

4. The method according to claim 3, wherein the queen plum extract enhances intestinal iron absorption.

* * * * *

SEQUENCE LISTING

```
Sequence total quantity: 10
SEQ ID NO: 1          moltype = DNA  length = 23
FEATURE               Location/Qualifiers
source                1..23
                      mol_type = other DNA
                      organism = synthetic construct
```

-continued

```
SEQUENCE: 1
aagaacaact tccacgaaaa ggg                                          23

SEQ ID NO: 2          moltype = DNA  length = 20
FEATURE               Location/Qualifiers
source                1..20
                      mol_type = other DNA
                      organism = synthetic construct
SEQUENCE: 2
ggctgggtca agcatagtgt                                              20

SEQ ID NO: 3          moltype = DNA  length = 19
FEATURE               Location/Qualifiers
source                1..19
                      mol_type = other DNA
                      organism = synthetic construct
SEQUENCE: 3
cggcggagga aaactgtct                                               19

SEQ ID NO: 4          moltype = DNA  length = 21
FEATURE               Location/Qualifiers
source                1..21
                      mol_type = other DNA
                      organism = synthetic construct
SEQUENCE: 4
tcggctgggt aagaaatctg a                                            21

SEQ ID NO: 5          moltype = DNA  length = 21
FEATURE               Location/Qualifiers
source                1..21
                      mol_type = other DNA
                      organism = synthetic construct
SEQUENCE: 5
agagtgtctg cggatacttc c                                            21

SEQ ID NO: 6          moltype = DNA  length = 21
FEATURE               Location/Qualifiers
source                1..21
                      mol_type = other DNA
                      organism = synthetic construct
SEQUENCE: 6
ccaacagtgt aggtcttggt g                                            21

SEQ ID NO: 7          moltype = DNA  length = 22
FEATURE               Location/Qualifiers
source                1..22
                      mol_type = other DNA
                      organism = synthetic construct
SEQUENCE: 7
tgtaccgcta tggttacact cg                                           22

SEQ ID NO: 8          moltype = DNA  length = 19
FEATURE               Location/Qualifiers
source                1..19
                      mol_type = other DNA
                      organism = synthetic construct
SEQUENCE: 8
ggcagggaca gttgcttct                                               19

SEQ ID NO: 9          moltype = DNA  length = 21
FEATURE               Location/Qualifiers
source                1..21
                      mol_type = other DNA
                      organism = synthetic construct
SEQUENCE: 9
atcaaccgga ggaatttccg t                                            21

SEQ ID NO: 10         moltype = DNA  length = 21
FEATURE               Location/Qualifiers
source                1..21
                      mol_type = other DNA
                      organism = synthetic construct
SEQUENCE: 10
caccaggacg accaggtttt c                                            21
```